United States Patent [19]

Heiber et al.

[11] Patent Number: 4,917,676
[45] Date of Patent: * Apr. 17, 1990

[54] USER-ACTIVATED TRANSDERMAL THERAPEUTIC SYSTEM

[75] Inventors: Werner Heiber, Bedford Hills; Robert Andriola, Putnam Valley, both of N.Y.; Paul Williams, Fairlawn, N.J.; Charles Ebert, Redwood City, Calif.

[73] Assignee: Ciba-Geigy Corporation, Ardsley, N.Y.

[*] Notice: The portion of the term of this patent subsequent to Mar. 27, 2007 has been disclaimed.

[21] Appl. No.: 251,016

[22] Filed: Sep. 27, 1988

Related U.S. Application Data

[63] Continuation of Ser. No. 933,000, Nov. 20, 1986, abandoned.

[51] Int. Cl.$^5$ ............................................. A61F 13/00
[52] U.S. Cl. ................................. 424/449; 604/306; 604/307; 424/448
[58] Field of Search ............... 604/896, 897, 890, 892, 604/87, 416, 304–308; 424/447–449; 128/156; 206/219, 221

[56] References Cited

U.S. PATENT DOCUMENTS

| | | | |
|---|---|---|---|
| 3,306,292 | 2/1967 | Spees | 128/156 |
| 3,565,075 | 2/1971 | Jerry | 128/156 |
| 3,580,254 | 5/1971 | Stuart | 128/156 |
| 3,702,677 | 11/1972 | Heffington | 239/55 |
| 3,797,492 | 3/1974 | Ploce | 604/890 |
| 4,320,759 | 3/1982 | Theeuwes | 604/892 |
| 4,449,983 | 5/1984 | Cortese et al. | 604/892.1 |
| 4,526,176 | 7/1985 | Bremer et al. | 128/641 |
| 4,608,043 | 8/1986 | Larkin | 604/87 |
| 4,635,624 | 1/1987 | Gilman | 128/156 |
| 4,645,502 | 2/1987 | Gale et al. | 604/896 |
| 4,666,441 | 5/1987 | Andriolo et al. | 604/897 |
| 4,687,476 | 8/1987 | Pailin | 128/156 |
| 4,693,706 | 9/1987 | Ennis, III | 604/87 |
| 4,693,711 | 9/1987 | Bremer et al. | 604/87 |
| 4,781,924 | 11/1988 | Lee et al. | 424/449 |

FOREIGN PATENT DOCUMENTS 992459 5/1965 United Kingdom ............... 206/219

Primary Examiner—C. Fred Rosenbaum
Assistant Examiner—Sharon Rose
Attorney, Agent, or Firm—Irving M. Fishman

[57] ABSTRACT

A transdermal drug delivery system which is manufactured in a pre-activated state for at least one of storage stability, manufacture safety, user safety, or control of release characteristic considerations and which is activated by a patient (or other person applying the system to the patient) just prior to or immediately after applying the system to the patient's skin is disclosed.

20 Claims, 1 Drawing Sheet

USER-ACTIVATED TRANSDERMAL THERAPEUTIC SYSTEM

This application is a continuation of application Ser. No. 933,000, filed 11/20/86, now abandoned.

FIELD OF THE INVENTION

The instant invention relates to improved transdermal drug delivery systems. In the systems of the invention, the active agent is in a form which (a) does not migrate beyond the limits of its reservoir, and/or (b) is less active, less toxic, and/or more stable than the form of the active agent which would otherwise be administered by the transdermal route until such time as the system is activated by the user. Activation is achieved by contacting an activating substance with the active agent reservoir and/or the active agent reservoir contents, which activating substance has been physically separated from the active agent and active agent reservoir.

BACKGROUND OF THE INVENTION

Transdermal drug delivery systems have, in recent years, become an increasingly important means of administering drugs. Such systems offer advantages which are clearly not achievable by other modes of administration such as avoidance of the gastro-intestinal tract and "first-pass" through the liver, application close to the site of action, sustained action which can readily be adjusted, etc. Clearly then, such systems will become of even greater significance in the future.

Typical transdermal systems currently known are disclosed in U.S. Pat. Nos. 3,598,122; 3,598,123; 3,742,951; 3,797,494; 3,948,254; 3,996,934; 4,284,444; and 4,597,961. These systems fall essentially into two catagories, the "matrix" resevoir type and the "membrane bag" reservoir type. Each type has some kind of backing material, a drug reservoir, and an adhesive. The backing material is inert to the drug (or drug formulation) and adhesive and does not permit any of the drug formulation to migrate through it.

In matrix type systems, the drug resevoir is a matrix in which the drug is dispersed and through which it may migrate by diffusion or microporous flow. The matrix material may simultaneously act as an adhesive as well; in which case only an occlusive, removeable covering is required to complete the system. When the matrix material is not an adhesive, a suitable adhesive is also necessary to mount the matrix on the backing material as well as to the removeable occlusive covering. Alternatives to adhesives to secure the "matrix" to the backing material and removeable occlusive covering include compression fitting and "hot melting" including thermal impulse and ultrasonic welding.

In "membrane bag" type systems, a drug permeable membrane is mounted on the backing layer to define a pouch (either by adhesive, compression fitting or hot melting) or two membranes are sealed together to define a "bag" which is mounted on the backing with a suitable adhesive. Adhesive is also required on the bag's surface distal to the backing layer to affix an occlusive removeable covering.

In each of these systems the drug contained in the system is, at all relevant times, capable of crossing all of the system components which would be interposed between the drug and the removeable, occlusive covering, or patients skin.

While these known systems are quite useful, they also have severe drawbacks and limitations to their use. One of the most important drawbacks of the known transdermal systems is intimately related to the properties which make the route of administration possible at all, the ability to permeate intact skin. Because the active agent can (or the formulation containing it permits it to) permeate intact skin and quite potent agents are being used, extreme caution must be used in the manufacturing process. Here, bulk quantities of potent agents are being utilized and even minor "accidents" can result in severe medical emergencies. Small amounts which contaminate clothes can find their way onto worker's skin and then into their bodies. As such workers deal with the drug on a frequent basis, unless the utmost care is taken, these people can receive many times the therapeutic dose of the active agent. This problem is of even greater concern when the active agent has a high vapor pressure resulting in vapor settling on clothes, uncovered skin or elsewhere.

Another problem of the known transdermal systems is that frequently the permeating form of the drug is not suitably stable; therefore, the shelf life of the system would be too short to be commercially practical. A third problem encountered by the known transdermal systems is the problem of "drug leakage", primarily through the adhesive. The drug must be able to migrate through or around the adhesive. Since it can, it will redistribute itself from the reservoir into the adhesive, and if the adhesive (and permeable membrane) have edges which are not surrounded by an occlusive covering, drug loss results.

In addition, transdermal systems of the art are limited to regulating drug delivery by only a few, very limited means; drug concentration, membrane or matrix material and thickness, and flux enhancers. However, once the parameters are chosen, only a single release rate results per system. The only exception to this is in the case where the adhesive between the reservoir and the removeable, occlusive covering absorbs a portion of the drug. In this case, an initial "burst" effect is observed. The amount of drug initially delivered is higher and then tapers off to a sustained release level.

Another problem encountered with known transdermal devices is how to know when it is time to change the device for a fresh one. Dosing of any medication, by almost any route of administration has largely been one of "approximately" and "trial and error". This is especially so with respect to ambulatory patients and long term medication.

Therefore, one of the objects of the invention is to provide a transdermal system which overcomes these and other defects.

It is an object of the invention to provide a transdermal system which can be manufactured with greater safety with a broader range of active agents than previously possible.

It is another object of this invention to provide a transdermal system which is less hazardous to the user during its application to the patients skin.

It is an additional object of the invention to provide a transdermal system which has greater storage stability than the known systems.

Another object of the invention is to provide a transdermal system whose release characteristics can be designed in a manner to allow a complex arrangement of drug delivery regimens in a single system.

A still further object of the invention is to provide a change in the device perceptible to the user to indicate the system no longer contains an adequate drug supply.

A still further object is to deliver topical drugs to a patient's skin in accordance with the foregoing objects.

SUMMARY OF THE INVENTION

These and other objects are achieved by the instant invention which is an improved transdermal system having at least two physically distinct reservoirs. In one reservoir is an activating substance. The second reservoir corresponds to the prior art reservoirs mentioned above. The barrier separating the reservoirs does not allow passage of the activating substance. That barrier is breached by action of the user just prior to or shortly after application of the system, whereby the activating substance activates the system. Upon activation of the system, the drug can migrate to and through the skin and carry out its function.

DETAILED DESCRIPTION OF THE DRAWINGS

Figure 1:
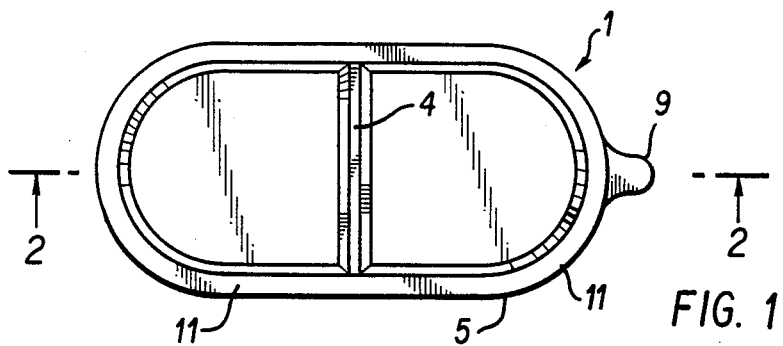
FIG. 1 is a top view of one embodiment of the invention having the respective reservoirs side by side.
Figure 2:
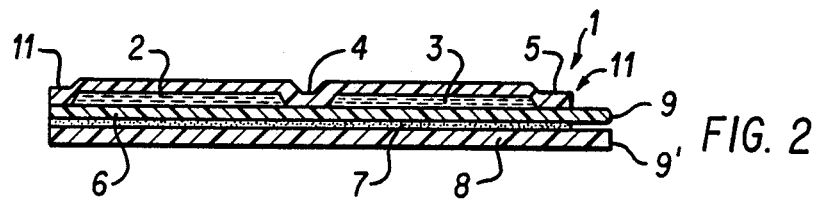
FIG. 2 is a cross-section view of FIG. 1 along line 2—2.

FIGS. 1 and 2 represent a first embodiment of the invention. As shown, the bottom most layer 8 is a removeable protective layer which is taken off transdermal patch 1 by a user or other person just prior to applying the remainder of the patch to a patient's skin. The remainder of the patch, comprising components 2–7 and 9 is applied to the patient as a unit, with first adhesive layer 7 contacting the skin. Adhesive layer 7 is also in contact with rate controlling membrane 6. Impermeable backing membrane 5 is sealed to rate controlled membrane 6, and together membranes 5 and 6 define two reservoir areas 2 and 3 therebetween. The two reservoir areas are separated by a pressure sensitive seal 4.

One of reservoir areas 2 and 3 contains an activating substance while the other contains a form of a therapeutic agent or a precursor thereof.

First tab 9' is a portion of the protective layer 8 which is not coated with adhesive and juts out from the rest of patch 1 so as to facilitate removal of protective layer 8. Second tab 9 is also not coated with adhesive and is used to remove the patch from the patient's skin.

This embodiment is typically prepared as follows: A silanized polyester (or other suitable material treated with a releasing agent), approximately 75 micron thick, is used as removable layer 8. Onto this is cast a contact adhesive, layer 7, typically a polyisobutylene solution. This is further laminated to a control membrane 6, if desired, about 100 microns thick. Ethylene-vinyl acetate is quite suitable for this membrane. Next, the contents of reservoirs 2 and 3 are dispensed, in a suitable form, on the rate controlling membrane and a suitable backing layer (about 80 micron) having a heat sealable coating on one surface is placed over the reservoir contants, coated side against the contents, and the device is heat sealed around the perimeter, seal 11, and between the two reservoirs, heat seal 4. The dimensions of heat seal 4 [preferably about 0.5 to about 2.0, more preferably about 0.5 to about 1.0 mm wide] and the seal(s) around the perimeter of the patch are such that seal 4 will selectively burst under pressure applied by the "user", advantageously at about 10 pounds of force to about 50 pounds of force. The minimum force to burst a burstable seal may be as high as about 20 pounds, preferably 17, more preferably 14, most preferably 10 pounds of applied force. Throughout this specification, and claims the term "applied force", unless otherwise characterized, means the total force ultimately translated to the burstable portions of the system.

As a practical matter, the burstable seal must be capable of bursting under pressures which will be commonly applied by those using or applying the system. Hence, a system having burstable seals which burst only upon an applied force in excess of 50 pounds is generally not suitable. However, seals which burst only at applied forces greater than 50 pounds, if desired, could certainly be used even though such systems might have limited patient acceptability. Preferably, the maximum applied force required to burst the burstable seal is about 40 pounds, more preferably 30 pounds, most preferably 20 pounds. The only real limitation within these bounds is that the non-burstable seals and membranes be capable of maintaining their integrity at the applied forces. Hence, such non-burstable seals and membranes must be of sufficient size and material to remain intact under pressures of at least 20 pounds to 60 pounds applied force. Preferably, the non-burstable portions of the system are of such size and materials so that they can withstand a force preferably at least 1.5, more preferably at least 2.0, most preferably 2.5, times that required to burst the burstable seal.

Figure 3:
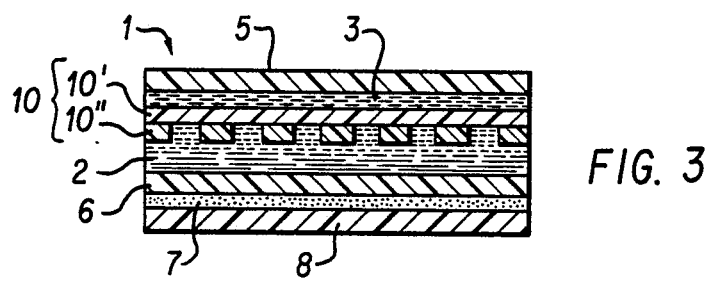
FIG. 3 is a cross-section of another embodiment of the invention having the reservoirs stacked, rather than side by side.

A second embodiment is shown in FIG. 3 (seal 11 and tabs 9 and 9' not being shown) wherein the reservoir areas are one on top of another and separated by pressure sensitive, non-permeable membrane 10. The pressure sensitive, non-permeable membrane 10 shown in this embodiment is prepared by laminating a perforated sheet of membrane material to a continuous sheet of membrane material, 10'; but it may also be a single layer continuous material which is unaltered or depth slit as desired. The limitations in the preceding paragraph regarding applied force are applicable here as well, pressure sensitive membrane 10 replacing burstable seal 4 in the description there. Advantageously, the continuous material is about 10 to about 50 microns and the perforated material independently about 10 to about 100 microns thick. More specifically, the continuous material is suitably 50, preferably 41, more preferably 33, and most preferably 25 microns thick; while the perforated material is suitably 100, preferably about 83, more preferably 66 and most preferably 50 microns thick. Alternatively, a continous sheet of material can be 'depth slit' to a suitable degree. These dimensions are given when the laminate membrane materials are ethylene/vinyl acetate copolymer. Use of different laminate materials having different strengths will lead to slightly different relative dimensions of thickness of the continuous and perforated materials. However, it should be realized that any degree of selectively re-inforcing only portions of the burstable membrane aid in the performance of the system.

The above laminate is placed over the contents of reservoir 2, with the weakened surface of the laminate preferably facing reservoir 2, the contents of reservoir 3 and backing layer 5 applied, and the entire assembly sealed.

Suitable alternative materials and dimensions for layers 5–9 are known in the transdermal art as apparent from the aforementioned U.S. patents. Layer 10 can be selected from any suitable membrane material which is known which can maintain a separation between the contents of reservoir 2 and reservoir 3. Most preferable layer 10 is a polyolefin (for example ethylene/vinyl acetate or polyethylene).

Alternative embodiments include those where rate controlling membrane 6 is either unnecessary or undesired and thus eliminated. In these situations, either reservoir 3 is a solid or a matrix containing the therapeutic agent. In another embodiment, reservoir 3 can be dispersed through an adhesive. In such an arrangement, membrane 6 is eliminated and reservoir 3 and adhesive 7 are a single layer.

In any event, when membrane 10 is present, the burstable membrane is no greater than about 20% to 80%, preferably about 20% to about 50% as thick as any other membrane made of the same material in the system.

Figure 4:
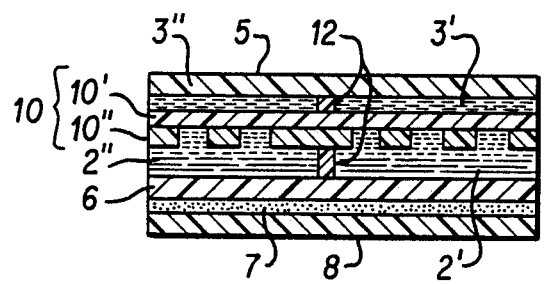
FIG. 4 is a cross-section of still another embodiment of the invention having more than the two reservoirs shown in the other Figures.

As one of ordinary skill will be aware, other embodiments include combinations of features of the foregoing embodiments. One such variation is the embodiment of FIG. 4. This differs from FIG. 3 in that reservoirs 2 and 3 have been split into two compartments each 2', 2'', 3' and 3'', by nonburstable, nonpermeable membranes (or nonburstable seals) 12. Membrane (or seal) 12 must meet the same requirements for nonburstability as set forth earlier for other nonburstable seals or membranes in the system. Such a system can be utilized to administer more than one therapeutic agent at a time when those agents are either chemically incompatable, require incompatable activating substances, cannot come in contact with the activating substance of the other therapeutic agent, or require different flux enhancers. Still other variations of contruction and utilities for the more complex systems will be apparent to those of ordinary skill.

A further variation of the embodiments described above is the inclusion of a user perceptible timing indicator to alert patients or those administering the patches to patients that the transdermal device has been exhausted, is near exhaustion, or is otherwise depleted to an extent that desired delivery characteristics are no longer being met. The timing device can be a nonpermeable ingredient which changes color over time once activation of the system has occurred, a nonpermeable colored ingredient which has been encapsulated with the encapsulating material degrading over time once activation has occurred, or most advantageously, a non-permeable color changing ingredient which color change results from the depletion of the active agent itself.

Generally, the user bursts the barrier (seal 4 or membrane 10) immediately before or after applying the patch to the skin. This now allows the contents of reservoirs 2 and 3 to come into contact, whereby the system is activated. Usually, the therapeutic agent is in a form which must be altered for the desired transdermal delivery and the activating substance transforms the therapeutic agent into the suitable species. However, it is not critical that the therapeutic agent be altered. It is only required that until the barrier between the reservoirs is breached, the system as a whole be in the inactive state. As such, systems wherein the activating substance alters the permeability characteristics of the layers between reservoir 2 and skin so that the unchanged therapeutic agent can then migrate to and through the skin are also within the scope of the invention.

As noted above, the critical feature of the invention is that until the activating substance is brought into contact with the inactive form of the therapeutic agent and/or the barrier between the therapeutic agent and the removeable occlusive layer or skin, the system is essentially inactive. Once this contact has been made, the system is activated and drug flow from the reservoir to the skin begins.

When a heat seal is used as the barrier between the reservoirs, heat seal 4 should be significantly thinner than the perimeter seals so that seal 4 is preferentially burst when placed under pressure. In order to insure that heat seal 4 doesn't inadvertantly burst under normal handling, it should be of sufficient thickness to resist pressures of up to about 5 to about 15 pounds applied force, preferably about 10 to about 15 pounds, more preferably 10 pounds of applied force. Advantageously, upon the application of forces in excess of about 5 to about 20, preferably about 10 to about 15, more preferably about 10, seal 4 will burst. However, seal 4 may resist greater forces, as set forth earlier, if desired.

When a membrane barrier is used, such as membrane 10, it can be constructed of the same or different materials as the other membranes of the system. If membrane 10 is of the same material as the other membranes, the unreinforced area should be significantly thinner than other membranes to insure selective bursting of barrier membrane 10. If desired, the reinforcing portion of barrier membrane 10 may be omitted, but it is most preferably present. If a different membrane material is selected for the unreinforced portion of barrier membrane 10, it can be of any appropriate thickness which will preferentially burst vis-a-vis the other membranes and seals when subjected to the applied forces in the range of 10 to 50 pounds as set out above. As noted above with respect to seal 4, barrier membrane 10, whether reinforced or not, must be resilient enough to resist bursting unintentionally under normal handling conditions.

There are a variety of "inactive" forms of the therapeutic agent and corresponding activating substance suitable for the instant invention. These include the therapeutic agent being a powder, a crystal, in an ionized form, being bound to an ion exchange resin or covalently coupled via labile linkages to an immobilizing moiety, being trapped in a polymer matrix, being encapsulated with an appropriate material or being in the form of a precursor or prodrug. Many other forms will be apparent to those of ordinary skill and are within the scope of the invention. Preferably this form of the therapeutic agent will not traverse the skin and/or at least one barrier of the system between the therapeutic agent and the skin (or removeable, protective layer 8). However, in the event one merely wishes to reduce the "hazards of manufacture and storage" these therapeutic agent forms may still be able to penetrate from the system into the skin before activation, but the activated form is the desired form to be administered. This may be exemplified by an application of an acidic drug, where the ionized species penetrates to a slight degree, but the free acid permeates through the appropriate barrier to a much larger degree and freely permeates through the skin. Upon application, but before activation, only a very low dose would be delivered. Upon activation, the much larger desired dose would reach the patient.

The activating substances are any appropriate substances which change the therapeutic agent form into one which will deliver the desired dose at the desired rate to the patient. These include solvents such as water, alcohol, etc; pH regulators such as buffers, acids, or bases; salt solutions to elute the drug; enzymes or catalysts to cleave labile linkages, swelling agents to open microencapsulation pores; appropriate reactive species to generate the drug from the prodrug or precursor; etc.

Figure 5:
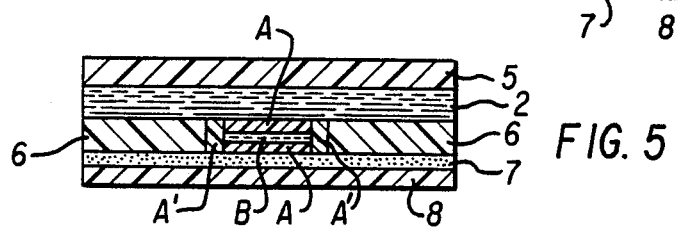
FIG. 5 is a cross-section of an embodiment of a membrane activation system according to the invention.

In other embodiments, the barrier between the drug and the skin (or removeable protective layer 8) is altered, instead of the therapeutic agent, to achieve activation. Such a system is exemplified by FIG. 5. In this Figure, permeable membrane 6 might be a xerogel or ionic gel which is not permeable to the drug or drug formulation until it is hydrated. Compartment B would contain water or buffer in a water impermeable casing of membrane A and A'. Depending upon the desired characteristics, activation could be achieved by selectively breaking the sidewalls of compartment B (walls A') and hydrating xerogel or increasing hydration of the ionic gel membrane 6. Once hydrated, the pores in membrane 6 will allow the passage of the drug in reservoir 3. A typical example is a crosslinked polyacrylic acid membrane 6 and a basic activating agent. When walls A' are broken, the polyacrylic acid pores open under the action of the basic activating agent so that the drug to be administered can migrate through the system.

While virtually any drug which can be administered transdermally (see for example U.S. Pat. Nos. 3,598,122; 3,598,123; 3,742,951; 3,797,494; 3,948,254; 3,996,934; 4,284,444; and 4,597,961; etc.) with the present system, it is especially useful to use the present invention to administer a drug selected from: antitubercular agents, such as isoniazid and rifampin; analgesics such as fentanyl and sufentanyl; muscle relaxants, such as baclofen; β-adrenergic receptor agonists and antiasthmatics, such as theophylline, formoterol, and terbutaline; steroids, such as estradiol, progesterone, methyltestosterone, and desoxycorticosterone; anticholinergics, such as scopolamine and methscopolamine; vasodilators, such as nitroglycerine; antihypertensives, such as metoprolol; antihistamines, such as triprolidine, tripelenamine, and diphenhydramine; cholinergic agents, such as arecoline; CNS stimulants, such as methylphenidate and nikethimide; angiotensin converting enzyme inhibitors, such as 3-(5-amino-1-carboxy)pentyl-amino]-1-carboxymethyl-2,3,4,5-tetrahydro-1H-1-benzazepine-2-one; nicotine, physostigmine, and naloxone. The only limitation to use of this system for a drug for transdermal use is that the drug have at least one form which permeates through the skin and any barriers of the system between the drug reservoir and the skin. If a topical drug is being administered, the only restriction is that there be at least one form of the drug which can migrate through the system barriers between the drug reservoir and the skin.

A preferred class of drugs for use in the system of the invention is: fentanyl, sufentanyl, terbutaline, formoterol, theophylline, estradiol, progesterone, scopolamine, nitroglycerine, triprolidine, tripelenamine, diphenhydramine, arecoline, nicotine, and 3-[(5-amino-1-carboxy)pentyl-amino]-1-carboxymethyl-2,3,4,5-tetrahydro-1H-1-benzazepine-2-one. A still more preferred group of drugs for use in the invention includes: arecoline, nicotine, progesterone, triprolidine, diphenhydramine, formoterol, scopolamine, nitroglycerine and estradiol. A most preferred drug for administration with the invention is selected from arecoline, nicotine, scopolamine, nitroglycerine and estradiol.

The invention will be further understood in connection with the following Examples which do not limit, but only exemplify, the invention.

EXAMPLE 1

This Example is based on FIGS. 1 and 2. The transdermal system described has an active drug releasing surface of 10 cm$^2$ and is manufactured according to the invention as follows: A polyisobutylene based contact adhesive dissolved in hexane is cast onto a 75 micron thick film of sylanized polyester. After drying of the adhesive, the adhesive side of the assembly is laminated to a 100 micron thick membrane of ethylene-vinyl acetate (EVA) copolymer leaving a strip at one side free of adhesive. The contents of reservoir 2, containing the drug, and reservoir 3, containing the base activator, are simultaneously dispensed side by side on the EVA copolymers side of the described laminate in the center of reservoirs 2 and 3. Reservoir 2 contains 183.6 mg of an Arecoline HBr Hydrobromide ointment consisting of 58.5% Arecoline HBr, 1.7% Carbopol 934P (as a gelling agent) and 39.8% of water. (183.6 mg of this ointment contains 107.4 mg or 0.455 mmole of Arecoline HBr). Reservoir 3 contains 121.3 mg of a potassium carbonate ointment consisting of 51.88% of Potassium carbonate, 1.57% of Carbopol 934P (as a gelling agent) and 46.58% of water. (121.3 mg of this ointment contains 62.39 mg or 0.455 mmole of potassium carbonate).

A 80 micron thick backing film (5) of polyester with an EVA heat sealable coating is laid over the dispensed portions of reservoir ointments 2 and 3, heat sealed at the perimeter and through the center, B, separating reservoirs 2 and 3. The perimeter consists of a non-destructive seal while seal 4 consists of a pressure sensitive seal breaking at 10 psi.

The system is activated by the user by bursting seal 4 and mixing the contents of reservoir 2 and 3. The membrane impermeable salt form of the drug is thus converted by the base activator into a membrane permeable form, the free base. The device has an active drug releasing surface of 10 cm$^2$ and delivers 22.5 mg of free base within 24 hours in vitro.

EXAMPLE 2

Solid Matrix

A transdermal drug delivery system according to the invention, as described in FIG. 3, is prepared as follows:

A solid matrix drug reservoir (3) is prepared by extruding poly-ethylene vinyl acetate (EVA) mixed with Arecoline Hydrobromide as an about 200 micron thick film, thus forming a porous monolithic matrix containing 50 to 60% drug by weight. Drug/polymer discs, corresponding to desired system surface areas, are then punched from the extruded film. A pressure sensitive membrane (10 in FIG. 3) is prepared by laminating a previously perforated EVA film (about 50 microns thick) with a continuous EVA film (about 10 microns thick) to form a net membrane laminate (60 microns thick) consisting of a structurally reinforced film with nonreinforced areas corresponding to the degree of perforation in the laminated film. As mechanical pressure is applied across the mebrane, the non-reinforced perfortion selectively ruptures. An alternate technique to prepare a weakened seam in a membrane is to depth slit an EVA membrane (about 70 microns thick) to produce structurally weakened points about 60 microns deep within the film. As pressure is applied across the film the controlled depth slit regions will selectively rupture. An activator ointment ("2" in FIG. 3) is dispensed onto the surface of the pressure sensitive membrane ("10" in FIG. 3) and a liquid form filled seal is made between the pressure sensitive membrane and a backing film ("5" in FIG. 3). A solid matrix drug/polymers disc ("3" in FIG. 3) is then positioned on the membrane surface of a rate controlling membrane/adhesive laminate (6 and 7 respectively) and an outer destructive seal is made between the rate controlling membrane ("6" in FIG. 3) through the pressure sensitive membrane ("10" in FIG. 3) to the backing layer. The system is activated by applying pressure to the top of backing film "5", thus rupturing pressure sensitive membrane "2". The activator ointment is then drawn into the solid drug/polymer matrix "3" by capillary tension and osmotic pressure, thereby converting impermeable Arcoline HBr to permeable Arecoline free base. Materials, drug forms, activators and rate control membranes described in the previous Example are applicable to this solid matrix system design.

We claim:

1. A therapeutic substance non-releasing drug delivery system having a removable protective layer thereon, said system comprising
    (a) a therapeutic substance reservoir containing a therapeutic agent or precursor of said therapeutic agent in a first form which cannot permeate from said therapeutic reservoir through said system to the surface of said system which is or was in contact with said removable protective layer;
    (b) an activating agent reservoir containing a system activating agent;
    (c) a burstable seal or membrane between (a) and (b) which is impermeable to said system activating agent and said therapeutic agent or precursor of said therapeutic agent; and
    (d) an occlusive backing layer; wherein upon bursting of said burstable seal or said burstable membrane, said system activating agent activates said system by contacting and converting said therapeutic agent or precursor of said therapeutic agent from said first form into a therapeutic agent second form which second form which migrates from said therapeutic agent or precursor of said therapeutic reservoir to said surface of said system which is or was in contact with said removable protective layer whereby said system becomes a therapeutic substance releasing delivery system.

2. A drug delivery system of claim 1 wherein said burstable membrane and burstable seal are broken by application of a pressure between about 10 and 50 pounds force.

3. A drug delivery system of claim 1 wherein said burstable membrane and burstable seal are a membrane and seal which selectively ruptured as compared to other membranes, seals and layers of said system under pressures of about 10 to about 50 pounds force.

4. A drug delivery system of claim 3 wherein said burstable seal is a heat seal which is no greater than about 1/6 as wide as any other heat seal of the same material in said system.

5. A drug delivery system of claim 3 wherein said burstable heat seal is from about 0.5 to about 2.0 mm wide.

6. A drug delivery system of claim 3 wherein said burstable membrane is selectively reinforced with unreinforced areas being no greater than about 20% to about 80% as wide as any other membrane or layer in said system made of the same material.

7. A drug delivery system of claim 6 wherein unreinforced areas of said burstable membrane are no greater than about 10 to about 50 microns thick.

8. A drug delivery system of claim 3 wherein said burstable membrane is a membrane which would otherwise not be burstable under normal use but which has been selectively weakened.

9. A drug delivery system of claim 8 wherein said burstable membrane has been made selectively burstable by controlled depth slitting.

10. A drug delivery system of claim 1 wherein said therapeutic agent is selected from fentanyl, sufentanyl, isoniazid, rifampin, baclofen, terbutaline, theophylline, arecoline, nicotine, progesterone, methyltestosterone, desoxycorticosterone, triprolidine, diphenylhydramine, tripelenamine, scopolamine, methscopolamine, nitroglycerin, metoprolol, estradiol, 3-([5-amino-1-carboxy]-pentylmino)-1-carboxy methyl-2,3,4,5-tetrahydro-1H-1-benzazepine-2-one, formoterol, physostigmine, and naloxone.

11. A therapeutic substance non-releasing drug delivery system having a removable protective layer thereon, said system comprising
    (a) therapeutic substance reservoir containing a therapeutic agent in a form which cannot permeate from said therapeutic reservoir through said system to the surface of said system which is or was in contact with said removable protective layer;
    (b) an activating agent reservoir containing a system activating agent;
    (c) a burstable membrane or burstable seal between said activating agent reservoir and the portions of said system through which said therapeutic agent must migrate in order to reach said surface which is or was in contact with said removable protective layer but through which said therapeutic agent cannot permeate; and
    (d) an occlusive backing layer; wherein, upon bursting of said burstable membrane or burstable seal, said activating agent activates said system by contacting said portions through which said therapeutic agent must migrate but cannot migrate to reach the surface of said system which is or was in contact with said removable protection layer and modifying such portions into a form through which said therapeutic agent migrates, whereby said therapeutic permeates through said system from said therapeutic reservoir to said surface of said system which is or was in contact with said removable protective layer and said system becomes a therapeutic substance releasing delivery system.

12. A drug delivery system of claim 11 wherein said burstable membrane and burstable seal are broken by application of a pressure between about 10 and 50 pounds force.

13. A drug delivery system of claim 11 wherein said burstable membrane and burstable seal are a membrane and seal which selectively rupture as compared to other membranes, seals and layers of said system, under pressures of about 10 to about 50 pounds force.

14. A drug delivery system of claim 13 wherein said burstable seal is a heat seal which is no greater than about 1/6 as wide as any other heat seal of the same material in said system.

15. A drug delivery system of claim 13 wherein said burstable heat seal is from about 0.5 to about 2.0 mm wide.

16. A drug delivery system of claim 13 wherein said burstable membrane is selectively reinforced with unreinforced areas being no greater than about 20% to about 80% as wide as any other membrane or layer in said system made of the same material.

17. A drug delivery system of claim 16 where said unreinforced areas of said burstable membrane are no greater than about 10 to about 50 microns thick.

18. A drug delivery system of claim 13 wherein said burstable membrane is a membrane which would otherwise not be burstable under normal use but which has been selectively weakened.

19. A drug delivery system of claim 18 wherein said burstable membrane has been made selectively burstable by controlled depth slitting.

20. A drug delivery system of claim 11 wherein said therapeutic agent is selected from fentanyl, sufentanyl, isoniazid, rifampin, baclofen, terbutaline, theophylline, arecoline, nicotine, progesterone, methyltestosterone, desoxycorticosterone, triprolidine, diphenylhydramine, tripelenamine, scopolamine, methscopolamine, nitroglyercine, metoprolol, estradiol, 3-([5-amino-1-carboxy]-pentylmino)-1-carboxy methyl-b 2,3,4,5-tetrahydro-1H-1-benzazepine-2-one, formoterol, physostigmine, and naloxone.

* * * * *